United States Patent [19]

Imai et al.

[11] 4,073,881
[45] Feb. 14, 1978

[54] CONDITIONING THE HAIR WITH A COMPOSITION CONTAINING A LIQUID POLYMER OF AN α-OLEFIN

[75] Inventors: Makoto Imai, Tokyo; Teruo Horiuchi, Sayama; Ichiro Kashiwa, Kokubunji, all of Japan

[73] Assignee: Lion Fat & Oil Co., Ltd., Tokyo, Japan

[21] Appl. No.: 663,735

[22] Filed: Mar. 4, 1976

[30] Foreign Application Priority Data

Mar. 20, 1975    Japan ................................. 50-33625

[51] Int. Cl.$^2$ .............................................. A61K 7/08
[52] U.S. Cl. ......................................... 424/70; 132/7; 252/DIG. 2; 252/DIG. 3; 260/29.6 XA; 424/DIG. 2; 424/365
[58] Field of Search .................... 424/DIG. 2, 70, 71, 424/168, 171, 365; 260/683.15 R, 683.15 A, 683.15 B, 29.6 XA; 252/DIG. 2, DIG. 3, 130, 542, 544, 546, 547, 50, 556, 551, 554, 555, 49.5; 132/7

[56] References Cited

U.S. PATENT DOCUMENTS

| | | | |
|---|---|---|---|
| 2,559,984 | 7/1951 | Montgomery et al. | 260/683.15 A |
| 2,595,140 | 4/1952 | Heinrich | 252/50 |
| 3,305,507 | 2/1967 | White et al. | 260/29.6 XA |
| 3,349,148 | 10/1967 | Bush | 260/683.15 B |
| 3,382,291 | 5/1968 | Brennan | 260/683.15 B |
| 3,642,676 | 2/1972 | Saunders et al. | 260/26.6 XA |
| 3,947,509 | 3/1976 | Isa et al. | 260/683.15 B |
| 3,957,664 | 5/1976 | Heilman et al. | 260/683.15 B |

FOREIGN PATENT DOCUMENTS 1,102,563    5/1955    France ................................. 424/71

*Primary Examiner*—Albert T. Meyers
*Assistant Examiner*—Vera C. Clarke
*Attorney, Agent, or Firm*—Blanchard, Flynn, Thiel, Boutell & Tanis

[57] ABSTRACT

Hair conditioner compositions suitable for use as after-shampoo preparations or before-shampoo preparations which comprise (A) 1 to 40% by weight of a liquid polymer that is obtained by polymerization of α-olefin having 6 to 18 carbon atoms and has an average of from 24 to 60 carbon atoms and a viscosity of 18 to 200 centistokes at 37.8° C (100° F), (B) 0.5 to 25% by weight of a surface active agent, and (C) 20 to 95% by weight of water.

11 Claims, No Drawings

CONDITIONING THE HAIR WITH A COMPOSITION CONTAINING A LIQUID POLYMER OF AN α-OLEFIN

BACKGROUND OF THE INVENTION a. Field of the Invention

The present invention relates to hair conditioner compositions which contain oil having a high percentage of deposit on hair and which are superior in their hair conditioning effects.

b. Description of the Prior Art

Various kinds of oil components have hitherto been utilized for the rinses used after shampooing and the conditioners used before shampooing so that the aforesaid products may attain the following conditioning effects, for instance, of supplying the lipids that are removed from hair by shampooing, forming a sort of oil film on the surface of hair, imparting luster, protecting hair from mechanical damage such as brushing and the like, relieving drying and brittleness of hair, and so forth. The oil components which have hitherto been used are higher alcohols, glycerides, higher fatty acids, lanolin derivatives, liquid paraffin, squalane, and so forth.

However, those oil components have a variety of disadvantages including, for example, the melting points of some of them are so high that formation of a uniform film becomes difficult, some of them have heavy oiliness so as to impart a greasy appearance to hair, some of them are inferior in miscibility with other oil substances, some of them are high-priced, some of them are irritating to skin, and the like. Those oil components have the common defect that, when they are utilized in after-shampoo preparations or before-shampoo preparations, they can achieve no satisfactory effects because even the oil component indispensable to hair is removed together with the excess oil component when rinsing hair with water or shampooing after they have been used.

SUMMARY OF THE INVENTION

The present invention has been accomplished through a series of investigations to overcome the above-mentioned disadvantages inherent to those prior art products, and relates to hair conditioner compositions which contain an oil having a high percentage of deposit to hair and which have an excellent hair-conditioning effect. The hair conditioner components according to the present invention are suitable for use as an after-shampoo preparation, especially one which requires rinsing with water after its use, as well as a before-shampoo preparation to be applied onto hair prior to shampooing. The oil content of the composition according to the present invention, which exhibits a high percentage of deposit to hair, is a liquid polymer that is obtained by polymerization of α-olefin having 6 to 18 carbon atoms and has an average of from 24 to 60 carbon atoms and a viscosity of 18 to 200 centistokes at 37.8° C (100° F).

DETAILED DESCRIPTION OF THE INVENTION

In the liquid polymer of the present invention the average of the total carbon atoms is 24 to 60, preferably 26 to 45, and more preferably 27 to 35.

In case the average number of carbon atoms is smaller than 24 it causs an undesirable result because the percentage of deposit to hair is reduced, and in case the average number of carbon atoms is greater than 60 it is also undesirable because the liquid polymer possesses increased oiliness and is sticky. The liquid polymer suitably has a viscosity of 18 to 200 centistokes at 37.8° C. The viscosity of the liquid polymer of α-olefin, even when its average number of carbon atoms remains unchanged, varies depending on manufacturing methods. When the viscosity is smaller than 18 centistokes, the percentage of deposit of the liquid polymer to hair lowers to thereby impede attainment of sufficient effects, and in case the viscosity is larger than 200 centistokes the liquid polymer possesses increased oiliness to thereby impart to hair a sticky feeling. Both cases, therefore, are unsuitable. the suitable quantity of the liquid polymer used is 1 to 30% by weight when used as after-shampoo preparation, and is 10 to 40% by weight when used as before-shampoo preparation. In both instances, when the quantity of the liquid polymer used is small the effect obtained is also small, and when the said quantity is large, unless rinsing is done with scrupulous care, the quantity of the liquid polymer deposited on the hair is so great that evaporation of moisture is suppressed extremely, thereby leaving the hair sticky or dull, and such a condition is unsuitable.

The starting α-olefin has 6 to 18 carbon atoms, preferably 6 to 14 carbon atoms. When an α-olefin having less than 6 carbon atoms is utilized the average branched chain length is too short to obtain products having a high percentage of deposit to hair, and at the same time the oiliness is too high to be usable. When an α-olefin having more than 18 carbon atoms is utilized the average branched chain length becomes long, whereby the deposition of the resulting products decreases. Especially, in view of the branched chain structure varying depending on manufacturing methods, when an α-olefin having more than 15 carbon atoms is dominant the liquid polymer obtained by coordinate anionic polymerization is not necessarily sufficient in respect of viscosity, oiliness or percentage of deposit, and therefore it is important that said α-olefin is well balanced with other components. The liquid polymer of α-olefin according to the present invention is prepared from an α-olefin having 6 to 18 carbon atoms, singly or in mixture, the α-olefin polymerizing by cationic polymerization using a Lewis acid catalyst, coordinate anionic polymerization using a Ziegler type catalyst or radical polymerization using a peroxide or heat, removing the catalyst used, the unreacted olefin and oligomers having less than 20 carbon atoms, and if required hydrogenating the double bond.

The liquid polymer that is used in the present invention has branched chains, has distribution at the position bonding to the main chain and the carbon atoms of the branched chains, and preferably has two or more of branched chains. The preferable manufacturing method is a cationic polymerization method by modified Lewis acid catalyst in which $AlX_3$ (X represents halogen) is used in combination with etherification, esterification, ether-esterification products of polyhydric alcohols or ketones and other components as occasion demands.

According to this method there can be obtained a liquid polymer of a mixture of various kinds of isomers which are of different structures respectively and the liquid polymer which is of a superior deposition, that is, a high percentage of deposit to hair, owing to an isomerization reaction which takes place simultaneously with the polymerization reaction. The liquid polymer having 24 to 60 carbon atoms to be obtained by the use of said modified Lewis acid catalyst can meet the viscosity condition of 18 to 200 centistokes at 37.8° C. The specific manufacturing conditions of the liquid polymer according to the present invention are disclosed, for instance, in Japanese Patent Application Nos. 11441/1974 (corresponding to U.S. Ser. No. 538,965, filed Jan. 6, 1975, now, U.S. Pat. No. 3,952,071), 20476/1974 (corresponding to U.S. Ser. No. 549,864, filed Feb. 14, 1975, now U.S. Pat. No. 3,947,509, 20477/1974 (Japanese Laid Open Publication No. 112303/1975), 138702/1974 (corresponding to U.S. Ser. No. 634,074, filed Nov. 21, 1975, now U.S. Pat. No. 3,997,623) and 11897/1975 (corresponding to U.S. Ser. No. 652,426, filed Jan. 26, 1976, now U.S. Pat. No. 3,997,622).

Surface active agents are indispensable for the purpose of homogeneously emulsifying or dispersing the oil components in the composition as well as promoting the uniform deposit of the oil component to hair. In the case of before-shampoo preparations there are used nonionic and/or anionic surface active agents. In the case of after-shampoo preparations cationic surface active agents are components indispensable therefor, and in case cationic surface active agents are not effective to the aforesaid homogenization nonionic surface active agents may be used as indispensable components. Except for combinations of anionic and cationic surface active agents, different kinds of surface active agents may be used in combination in place thereof.

As the cationic surface active agents which are available in the present invention there can be enumerated dialkyl dimethyl ammonium salt-, alkyl trimethyl ammonium salt-, alkyl dimethyl benzyl ammonium salt-, alkyl imidazolinium salt-type cationic surface active agents, etc. having $C_{10}$- $C_{20}$ alkyl radicals. As the nonionic surface active agents which are useful in the present invention there can be enumerated $C_{10}$- $C_{22}$ aliphatic alcohol ethoxylates (average degree of polymerization $n = 2 - 25$), alkyl phenol ethoxylates ($n = 2 -$ ) having $C_6 - C_{15}$ alkyl radical, sorbitan esters of $C_{10} - C_{22}$ fatty acids and ethoxylates thereof ($n = 2 - 25$), cane sugar esters of $C_{10} - C_{22}$ fatty acids, etc. As the anionic surface active agents which are useful in the present invention there can be enumerated Na salts, K salts and alkanol amine salts of $C_8 - C_{20}$ fatty acids, $C_8 - C_{20}$ aliphatic alkyl sulfates and $C_8 - C_{22}$ aliphatic alcohol ethoxy sulfates ($n = 1 - 5$), and Na salts, K salts, Mg salts, Ca salts and alkanol amine salts of $\alpha$-olefin sulfonates. The quantity of the surface active agent used is suitably in the range of from 0.5 to 25% by weight. And in the case of the after-shampoo preparation there are used 0.5 to 10% by weight of cationic surface active agent as the softener, and if required 0.5% by weight or more, preferably 10% by weight or less, of nonionic surface active agent as the emulsifying agent. On the other hand, in the case of the before-shampoo preparation there are used 1 to 25% by weight, preferably 1 to 15% by weight, of nonionic and/or anionic surface active agents.

Water is an indispensable component of the hair conditioner composition according to the present invention from the two reasons that water is used in rinsing or shampooing after use of said composition and water is conveniently used. The appropriate quantity of water used is in the range of from 20 to 95% by weight and in the case of a before-shampoo preparation is in the range of from 20 to 89.5% by weight.

The hair conditioner composition of the present invention has the above-mentioned three components as indispensable components, and additionally may contain, according to the purpose and use, mono or trihydric lower alcohols such as ethanol, isopropanol, propylene glycol, glycerine, propylene glycol monoethyl ether, and the like, oil substances such as squalane, lanoline, higher alcohol, higher fatty acid and its lower alcohol ester, tripalmitin, olive oil, and so on, perfume, coloring materials, antioxidant, antibiotics, etc.

The hair conditioner of the present invention having such a composition as mentioned above can possess a high percentage of deposit to hair to thus attain excellent conditioning effects, for instance, natural glossy lustre, easy comb-through and prevention of hair from falling out due to its protective film of hair against mechanical damages such as brushing and the like, smoother and softer, etc., and furthermore it does not leave hair sticky. Especially, it is conspicuously superior in the smoother and softer touch compared with other oil components.

In the case of a before-shampoo preparation, hitherto used oil substances are not so effective because the greater part of them is removed at the time of shampooing, while the hair conditioner of the present invention can exhibit a conspicuously superior effect thereover. In the case of an after-shampoo preparation compounded with a cationic surface active agent there can be of course obtained softness, antistatic effect, sterilizing effect, etc.

The reason why such excellent effects can be obtained by the use of the hair conditioner of the present invention may be explained by considering that the liquid polymer of $\alpha$-olefin used in the present invention has a good affinity to skin and hair and therefore exhibits a high percentage of deposit to hair even when hair is washed with water. The reason therefor is unknown, but when taking account of the structure of the liquid polymer of $\alpha$-olefin it seems to be connected with the fact that the chain length of the alkyl radical branched from the main chain has a certain distribution. Because the liquid polymer deposited to hair does form a substantially uniform film on the surface of hair and further has a strong affinity to hair, there can be obtained not a greasy lustre but rather a glossy lustre on hair, and still further evaporation of moisture from hair is controlled to thereby produce a smoother and softer touch on hair and minimize the frictional force applied thereon.

Example for synthesis of the liquid polymer of $\alpha$-olefin

In an autoclave of 1 l volume made of glass provided with a stirrer there were placed 14.3 g of aluminum chloride and 7.8 g of ethylene glycol acetate; the mixture was heated to a temperature of from 120° to 130° C; 5 hour's polymerization was conducted while gradually adding thereto 600 g of octene-1 dropwise; thereafter the used catalyst was made inert; said catalyst, unreacted olefin and dimer were removed from the product; and the polymer was further subjected to hydrogenation, thereby obtaining a saturated liquid polymer in the yield of about 85%. The resulting liquid polymer was analyzed to have a viscosity of 21.5 centistokes at 37.8° C (100° F), an average molecular weight of about 370 and about 27 carbon atoms.

By using a similar procedure there can be obtained a liquid polymer having an average carbon chain length of from 24 to 60.

REFERENCE EXAMPLE 1

The amount of each of the oil components as shown in Table-1 deposited on the shampooed hair was compared according to the procedure in which each of the oil components in Table-1 was applied on hair in the ratio of 5 g to 100 g of hair, about 3 minutes' massage was conducted in order to make the oil component well permeate the hair; the hair was washed one time with tepid water (about 40°C); thereafter the hair was shampooed in the usual manner for 1 minute by means of a liquid shampoo which had a loading ratio of 1/20 and a concentration of 5%; the hair was washed twice with tepid water; and thereafter the hair was dried, then the oil still remaining on the hair was extracted with a solvent. The amount of the oil component deposited on hair was calculated on the basis of the liquid paraffin (SUS 70 sec) rated as 100. The results thus obtained are as shown in Table-1. In the case of the liquid paraffin the amount deposited on the hair after shampoo was calculated as 0.9 g to 100 g of hair.

Table-1

| Amounts of oil components deposited on shampooed hair | | |
| --- | --- | --- |
| Oil components | | Deposited amounts |
| Liquid polymer | (produced by the above synthesis example) | 360 |
| Liquid paraffin | (SUS 70 sec) | 100 |
| Cetyl alcohol | | 117 |
| Tristearin | | 133 |

REFERENCE EXAMPLE 2

The amount of each of the oil components as shown in Table-2 deposited on the shampooed and still wet hair was compared according to the procedure in which each of the oil components in Table-2 was applied on the shampooed and still wet hair in the ratio of 10 g to 100 g (weight of hair in the dried state); about 2 minutes' hair massage was conducted; thereafter hair was rinsed with tepid water; and hair was dried and the deposited oil was extracted with a solvent.

The amount of the oil component deposited on hair was calculated on the basis of the liquid paraffin (SUS 70 sec) rated as 100. The results thus obtained are as shown in Table-2. The amount of the liquid paraffin deposited on hair was 1.4 g to 100 g of hair.

Table -2

| Amounts of oil components deposited onto hair | | |
| --- | --- | --- |
| Oil components | | Deposited amount |
| Liquid polymer | (produced by the above synthesis example) | 180 |
| Liquid paraffin | (SUS 70 sec) | 100 |
| Squalane | | 120 |
| Cetyl alcohol | | 170 |
| Lanolin | | 165 |

EXAMPLE

By the use of various kinds of liquid polymers containing the liquid polymer according to the synthesis example there were prepared cream rinse compositions as shown in Table-3 and before-shampoo treatment compositions as shown in Table-4. The unit % is by weight.

Table -3

| Component | Cream rinse composition | | | | | | |
| --- | --- | --- | --- | --- | --- | --- | --- |
| | I | II | III | IV | V | VI | VII |
| Dialkyl dimethyl ammonium chloride | 2 | 3 | 4 | 3 | | 3 | 3 |
| Alkyl dimethyl benzyl ammonium chloride | | | | | 3 | | |
| Liquid polymer A | 20 | 5 | 2 | | | | |
| Liquid polymer B | | | | 10 | | | |
| Liquid polymer C | | | | | 5 | | |
| Liquid paraffin (SUS 70 sec) | | | | | | 5 | |
| Cetyl alcohol | | | | | | | 5 |
| Polyoxyethylene cetyl ether (p=7) | 6 | 4 | 3 | 4 | 4 | 4 | 4 |
| Propylene glycol | | | 5 | | | | |
| Ethanol | 10 | | | | 5 | | |
| Water | balance | balance | balance | balance | balance | balance | balance |
| Effects after use — Lustre | | | | △ | | △ | X |
| Effects after use — Combing | | | | | | | |
| Effects after use — Touch | | | | △ | | X | X |

(Note 1)
Liquid polymer A: a polymer prepared according to the synthesis example having a viscosity of 21.5 centistokes (37.8° C).
Liquid polymer B: a polymer prepared using $C_6 - C_{10}$ α-olefin according to the synthesis example which has a viscosity of 40 centistokes (37.8° C).
Liquid polymer C: a polymer prepared using $C_6 - C_{10}$ α-olefin according to the synthesis example which has a viscosity of 100 centistokes (37.8° C).
(Note 2)
Estimation of effects:   denotes "very good"
△ denotes "fairly good"
X denotes "bad"
(Note 3)
The word "touch" implies an all-round estimation taking a smooth and soft feeling into consideration.

Table-4

| Component | Before-shampoo treatment composition | | | | | |
| --- | --- | --- | --- | --- | --- | --- |
| | I | II | III | IV | V | VI |
| Liquid polymer A | 40 | 20 | | | | |
| Liquid polymer B | | | 25 | | | |
| Liquid polymer C | | | | 25 | | |
| Palmitic acid | 5 | 8 | 8 | 8 | 5 | 5 |
| Tripalmitin | 3 | 6 | 5 | 5 | 3 | 3 |

Table-4-continued

| Component | Before-shampoo treatment composition | | | | | |
|---|---|---|---|---|---|---|
| | I | II | III | IV | V | VI |
| Cetyl palmitate | 3 | 6 | 5 | 5 | 3 | 3 |
| Liquid paraffin | | | | | 40 | |
| Squalane | | | | | | 40 |
| Polyoxyethylene nonyl phenyl ether ($\bar{p}=5$) | 3 | 5 | | 3 | 3 | 3 |
| Triethanol amine soap | | | 4 | | | |
| Water | balance | balance | balance | balance | balance | balance |
| Effects after use — Lustre | | | | | Δ | Δ |
| Effects after use — Combing | | | | | | |
| Effects after use — Touch | | | | | X | Δ |

(Note 1) Explanations on the liquid polymers A, B and C in the case of the cream rinse composition are also applicable to the liquid polymers A, B and C in this case.
(Note 2) Estimation of the effects after use is same with that in the case of the cream rinse composition.

What is claimed is:

1. The method of conditioning hair for improving the lustre, combability and feel thereof which comprises the step of applying to hair an effective amount of the hair conditioner composition which comprises (A) from 1 to 40 weight percent of a liquid polymer having an average of from 24 to 60 carbon atoms and a viscosity of from 18 to 200 centistokes at 37.8° C, said liquid polymer having been prepared by cationic polymerization of an α-olefin having from 6 to 14 carbon atoms, in the presence of a Lewis acid catalyst consisting essentially of (a) an aluminum halide of the formula $AlX_3$ wherein X is halogen and (b) an etherified, esterified or etherified-esterified polyhydric alcohol or ketone, followed by removal of the catalyst and substances having less than 20 carbon atoms, (B) from 0.5 to 25 weight percent of a surface active agent effective for homogeneously emulsifying or dispersing component (A), said surface active agent being selected from the group consisting of anionic organic surfactants, nonionic organic surfactants, cationic organic surfactants and mixtures thereof, with the proviso that the composition does not contain both an anionic organic surfactant and a cationic organic surfactant, and (C) from 20 to 95 weight percent of water.

2. The method according to claim 1 in which said liquid polymer has an average of from 26 to 45 carbon atoms.

3. The method according to claim 1 in which said liquid polymer has an average of from 27 to 35 carbon atoms.

4. The method according to claim 1 in which said liquid polymer has two or more branched chains.

5. The method of conditioning hair for improving the lustre, combability and feel thereof, which comprises the step of applying to freshly washed hair an effective amount of the hair conditioner composition which comprises (A) from 1 to 30 weight percent of a liquid polymer having an average of from 24 to 60 carbon atoms and a viscosity of from 18 to 200 centistokes at 37.8° C, said liquid polymer having been prepared by cationic polymerization of an α-olefin having from 6 to 14 carbon atoms, in the presence of a Lewis acid catalyst consisting essentially of (A) an aluminum halide of the formula $AlX_3$ wherein X is halogen and (b) an etherified, esterified or etherified-esterified polyhydric alcohol or ketone, followed by removal of the catalyst and substances having less than 20 carbon atoms, (B) from 0.5 to 10 weight percent of a cationic organic surfactant effective for homogeneously emulsifying or dispersing component (A), and (C) from 20 to 95 weight percent of water.

6. The method according to claim 5 wherein said cationic organic surfactant is selected from the group consisting of dialkyl dimethyl ammonium salts, alkyl trimethyl ammonium salts, alkyl dimethyl benzyl ammonium salts and alkyl imidazolium salts, wherein each of said alkyls has 10 to 20 carbon atoms.

7. The method of conditioning hair for improving the lustre, compability and feel thereof, which comprises the step of applying to freshly washed hair an effective amount of the hair conditioner composition which comprises (A) from 1 to 30 weight percent of a liquid polymer having an average of from 24 to 60 carbon atoms and a viscosity of from 18 to 200 centistokes at 37.8° C, said liquid polymer having been prepared by cationic polymerization of an α-olefin having from 6 to 14 carbon atoms, in the presence of a Lewis acid catalyst consisting essentially of (a) an aluminum halide of the formula $AlX_3$ wherein X is halogen and (b) an etherified, esterified and etherified-esterified polyhydric alcohol or ketone, followed by removal of the catalyst and substances having less than 20 carbon atoms, (B) from 0.5 to 10 weight percent of a cationic organic surfactant and from 0.5 to 10 weight percent of a nonionic organic surfactant effective for homogeneously emulsifying or dispersing component (A), and (C) from 20 to 95 weight percent of water.

8. The method according to claim 7 wherein said cationic organic surfactant is selected from the group consisting of dialkyl dimethyl ammonium salts, alkyl trimethyl ammonium salts, alkyl dimethyl benzyl ammonium salts and alkyl imidazolinium salts, wherein each of said alkyls has 10 to 20 carbon atoms, and wherein said nonionic organic surfactant is selected from the group consisting of $C_{10}$–$C_{22}$ aliphatic alcohol ethoxylates having from 2 to 25 ethoxy units, alkyl ($C_6$–$C_{15}$) phenol ethoxylates having from 2 to 25 ethoxy units, sorbitan esters of $C_{10}$–$C_{22}$ fatty acids ethoxylates of sorbitan of $C_{10}$–$C_{22}$ fatty acids having from 2 to 25 ethoxy units and cane sugar esters of $C_{10}$–$C_{22}$ fatty acids.

9. The method of conditioning hair before shampooing the same for improving the lustre, compability and feel thereof which comprises applying to the hair an effective amount of the hair conditioner composition which comprises (A) from 10 to 40 weight percent of a liquid polymer having an average of from 24 to 60 carbon atoms and a viscosity of from 18 to 200 centistokes at 37.8° C, said liquid polymer having been prepared by cationic polymerization of an α-olefin having from 6 to 14 carbon atoms, in the presence of a Lewis acid catalyst consisting essentially of (a) an aluminum halide of the formula $AlX_3$ wherein X is halogen and (b) an etherified, esterified or etherified-esterified polyhydric alcohol or ketone, followed by removal of the catalyst and substances having less than 20 carbon atoms, (B) from 1 to 25 weight percent of a surface active agent effective for homogeneously emulsifying or dispersing component (A), said surface active agent being selected from the group consisting of anionic organic surfactants, nonionic organic surfactants and mixtures thereof, and (C) from 20 to 95 weight percent of water.

10. The method according to claim 9 wherein said nonionic organic surfactant is selected from the group consisting of $C_{10}$–$C_{22}$ aliphatic alcohol ethoxylates having from 2 to 25 ethoxy units, alkyl ($C_6$–$C_{15}$) phenol ethoxylates having from 2 to 25 ethoxy units, sorbitan esters of $C_{10}$–$C_{22}$ fatty acids, ethoxylates of sorbitan exters of $C_{10}$–$C_{22}$ fatty acids containing from 2 to 25 ethoxy units and cane sugar esters of $C_{10}$–$C_{22}$ fatty acids, and wherein said anionic organic surfactant is selected from the group consisting of sodium, potassium and alkanolamine salts of $C_8$–$C_{20}$ fatty acids, $C_8$–$C_{20}$ alkyl sulfates and $C_8$–$C_{22}$ aliphatic alcohol ethoxy sulfates containing 1 to 5 ethoxy units, and sodium, potassium, magnesium, calcium and alkanolamine salts of α-olefin sulfonates.

11. The method according to claim 10 wherein the amount of said surface active agent is from 1 to 15 weight percent.

* * * * *

UNITED STATES PATENT AND TRADEMARK OFFICE
CERTIFICATE OF CORRECTION

PATENT NO. : 4 073 881
DATED : February 14, 1978
INVENTOR(S) : Makoto Imai et al It is certified that error appears in the above-identified patent and that said Letters Patent are hereby corrected as shown below:

Column 8, line 21; change "compability" to ---combability---.

Column 8, line 54; change "compability" to ---combability---.

Column 9, line 12; change "exters" to ---esters---.

Signed and Sealed this

Sixth Day of June 1978

[SEAL]

Attest:

RUTH C. MASON
*Attesting Officer*

DONALD W. BANNER
*Commissioner of Patents and Trademarks*